(12) United States Patent
Waldenburg

(10) Patent No.: US 7,517,691 B2
(45) Date of Patent: Apr. 14, 2009

(54) DEVICE FOR AND METHOD OF TESTING OCCULT BLOOD IN FECES

(76) Inventor: Ottfried Waldenburg, 3910 Placita Sabino, Tucson, AZ (US) 85749

( * ) Notice: Subject to any disclaimer, the term of this patent is extended or adjusted under 35 U.S.C. 154(b) by 21 days.

(21) Appl. No.: 11/856,511

(22) Filed: Sep. 17, 2007

(65) Prior Publication Data
US 2008/0070313 A1     Mar. 20, 2008

Related U.S. Application Data

(63) Continuation of application No. 10/513,879, filed as application No. PCT/US03/15163 on May 13, 2003, now abandoned.

(60) Provisional application No. 60/380,372, filed on May 14, 2002.

(51) Int. Cl.
*G01N 33/52* (2006.01)
*G01N 33/72* (2006.01)
*G01N 21/78* (2006.01)

(52) U.S. Cl. ............... 436/66; 436/63; 436/135; 436/164; 436/169; 422/55; 422/56; 422/58; 422/68.1; 600/562; 600/572

(58) Field of Classification Search ........... 436/63, 436/66, 135, 164, 169; 422/55, 56, 58, 61, 422/68.1; 600/562, 572
See application file for complete search history.

(56) References Cited

U.S. PATENT DOCUMENTS

| 4,559,949 A |    | 12/1985 | Levine              |         |
|-------------|----|---------|---------------------|---------|
| 4,578,358 A |    | 3/1986  | Oksman et al.       |         |
| 4,582,685 A |    | 4/1986  | Guadagno et al.     |         |
| 4,645,743 A |    | 2/1987  | Baker et al.        |         |
| 4,675,160 A | *  | 6/1987  | Talmage et al.      | 422/53  |
| 4,725,553 A | *  | 2/1988  | Guadagno            | 436/66  |
| 4,804,518 A |    | 2/1989  | Levine et al.       |         |
| 5,217,874 A | *  | 6/1993  | Guadagno et al.     | 435/28  |
| 5,747,344 A |    | 5/1998  | Cleator             |         |
| 5,840,584 A |    | 11/1998 | Waldenburg          |         |
| 6,436,714 B1|    | 8/2002  | Clawson et al.      |         |

FOREIGN PATENT DOCUMENTS

WO     WO/03/098224 A1    11/2003

OTHER PUBLICATIONS

PCT Notice Of Transmittal of Intl. Search Report PCT/US03/15163.
U.S. Board Of Patent Appeals, Decision On Appeal.

* cited by examiner

*Primary Examiner*—Maureen M Wallenhorst
(74) *Attorney, Agent, or Firm*—John J. Connors; Connors & Assoc, Inc.

(57) ABSTRACT

The presence of occult blood in feces is detected using device including a liquid tight packet containing a sheet of absorbent material impregnated with a liquid solution that reacts with feces to produce a color change when blood is present. The packet is opened manually by tearing the packet apart to access the sheet absorbent material, which is then used to collecting a sample of feces on the impregnated sheet of absorbent material.

6 Claims, 2 Drawing Sheets

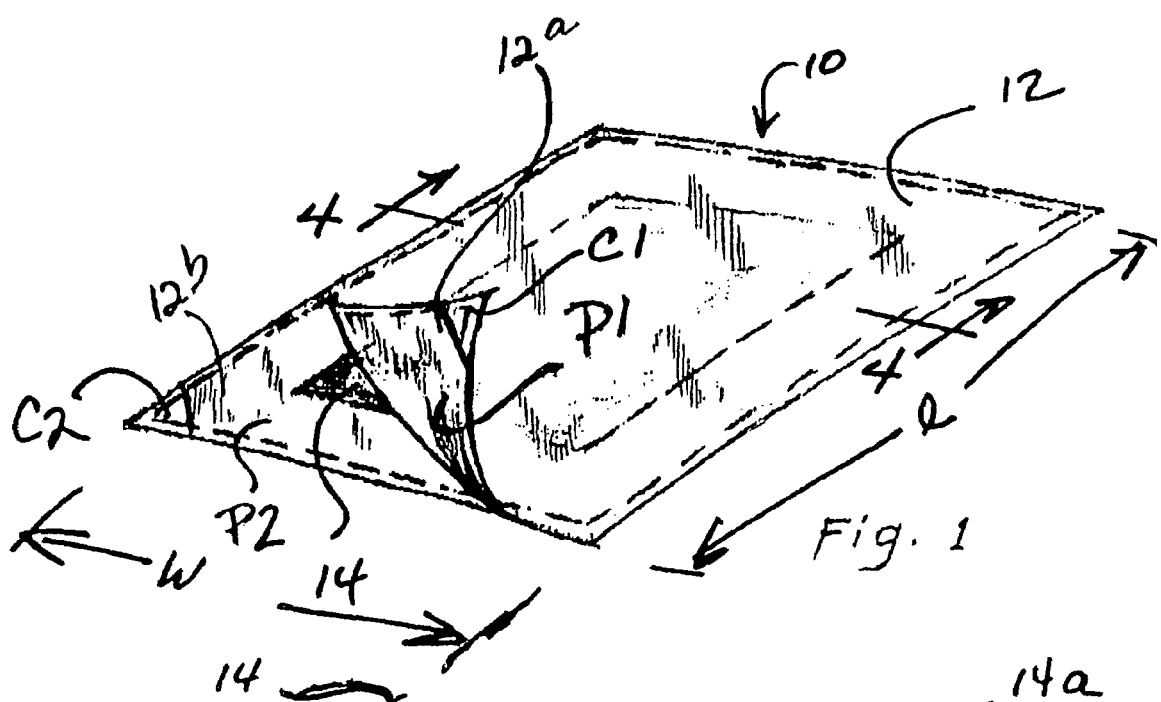
Fig. 1
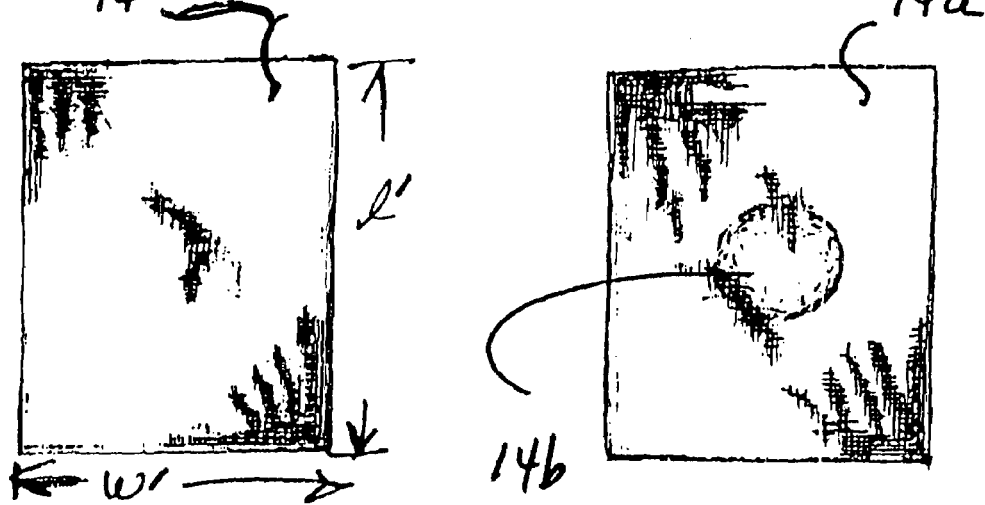 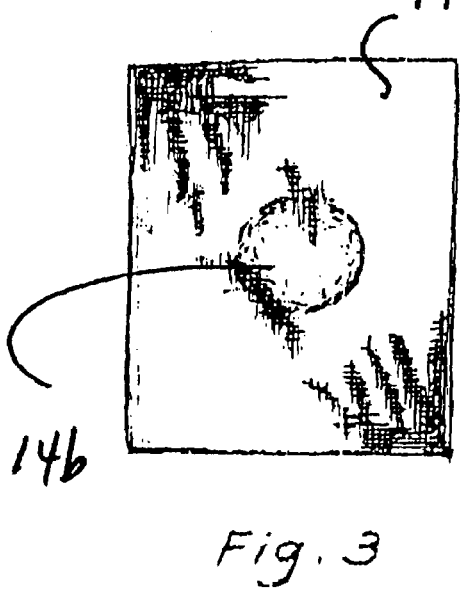
Fig. 2   Fig. 3

DEVICE FOR AND METHOD OF TESTING OCCULT BLOOD IN FECES

INCORPORATION BY REFERENCE

This application is a continuation of U.S. patent application Ser. No. 10/513,879, filed Nov. 9, 2004, now abandoned, which claims the benefit under 35 USC §371 of International Application No. PCT/US0315163, entitled "DEVICE FOR & METHOD OF TESTING OCCULT BLOOD IN FECES," filed May 13, 2003, which claims the benefit under 35 USC 119(e) of U.S. provisional patent Application No. 60/380,372, entitled "Device For & Method Of Testing Occult Blood In Feces," filed May 14, 2002. All of these related applications are incorporated herein by reference and made a part of this application. Moreover, any and all U.S. patents, U.S. patent applications, and other documents, hard copy or electronic, cited or referred to in this application are incorporated herein by reference and made a part of this application.

DEFINITIONS

The words "comprising," "having," and "including," and other forms thereof, are intended to be equivalent in meaning and be open ended in that an item or items following any one of these words is not meant to be an exhaustive listing of such item or items, or meant to be limited to only the listed item or items.

BACKGROUND OF INVENTION

The inventor in U.S. Pat. No. 5,840,584 disclosed a device for testing the presence of occult blood in feces using the following reactants: (1) a solution of guaiac material and (2) hydrogen peroxide. This device holds the two types of reactants used in this test in separate chambers that are broken to mix the reactants together on an absorbent material at the time the test is preformed. A blue color appearing on the absorbent material indicates the presence of occult blood in feces.

SUMMARY OF INVENTION

This invention has one or more features as discussed subsequently herein. After reading the following section entitled "DETAILED DESCRIPTION OF SOME EMBODIMENTS OF THIS INVENTION," one will understand how the features of this invention provide its benefits. The benefits of this invention include, but are not limited to, providing a low cost disposable device that is easy to manufacture and convenient of use, avoiding the mess typically associated with occult blood in feces tests.

Without limiting the scope of this invention as expressed by the claims that follow, some, but not necessarily all, of its features are:

One, a device of this invention is used to detect the presence of occult blood in feces. It comprises liquid tight packet that is opened manually by tearing the packet. The packet contains a sheet of absorbent material impregnated with a liquid solution that reacts with feces to produce a color change when blood is present. The solution may include guaiac material and hydrogen peroxide. Typically, the sheet of absorbent material is tissue paper.

Two, the packet may be evacuated to remove air therefrom and sealed to prevent the liquid solution from escaping the packet until opened to use the impregnated sheet of absorbent material. Typically, the packet is made of a substance that is essentially impermeable to light and air, usually aluminum foil having a thickness of less than about 1/16 inch.

Three, the packet may comprise two overlying impermeable layers of about the same size and shape, typically square or rectangular, with a sheet of tissue paper sandwiched between them. The layers may each have outer edge portions defining a layer's perimeter. The overlapping outer edge portions of the layers are adjoined together and sealed to prevent the liquid solution from escaping the packet until opened to use the impregnated sheet of tissue paper. If done in the presence of a detrimental substance, this substance may be removed prior to sealing. For example, any air between the layers may be evacuated therefrom by vacuum prior to sealing.

Four, the liquid solution may comprises from about 3 to about 8 weight percent hydrogen peroxide, from about 60 to about 80 weight percent alcohol, and from about 12 to about 37 weight percent guaiac material.

These features are not listed in any rank order nor is this list intended to be exhaustive.

This invention also includes a method of detecting the presence of occult blood in feces. This method comprise the steps of (a) providing a packet containing a sheet of absorbent material impregnated with a liquid solution that reacts with feces to produce a color change when blood is present, and (b) opening the packet and removing the impregnated sheet of absorbent material, and (c) collecting a sample of feces on the impregnated sheet of absorbent material, a color change appearing on the impregnated sheet of absorbent material in the presence of occult blood. The packet may be like that discussed above.

DESCRIPTION OF DRAWING

Some embodiments of this invention, illustrating all its features, will now be discussed in detail. These embodiments depict the novel and non-obvious device and method of this invention as shown in the accompanying drawings, which are for illustrative purposes only. These drawings includes the following figures (Figs.), with like numerals indicating like parts:

FIG. 1 is a perspective view of the device of this invention used in testing for occult blood in feces.

FIG. 2 is a plan view of one type of sheet of absorbent material used in this invention.

FIG. 3 is a plan view of a second type of sheet of absorbent material used in this invention.

DETAILED DESCRIPTION OF SOME EMBODIMENTS OF THIS INVENTION

Figure 4:
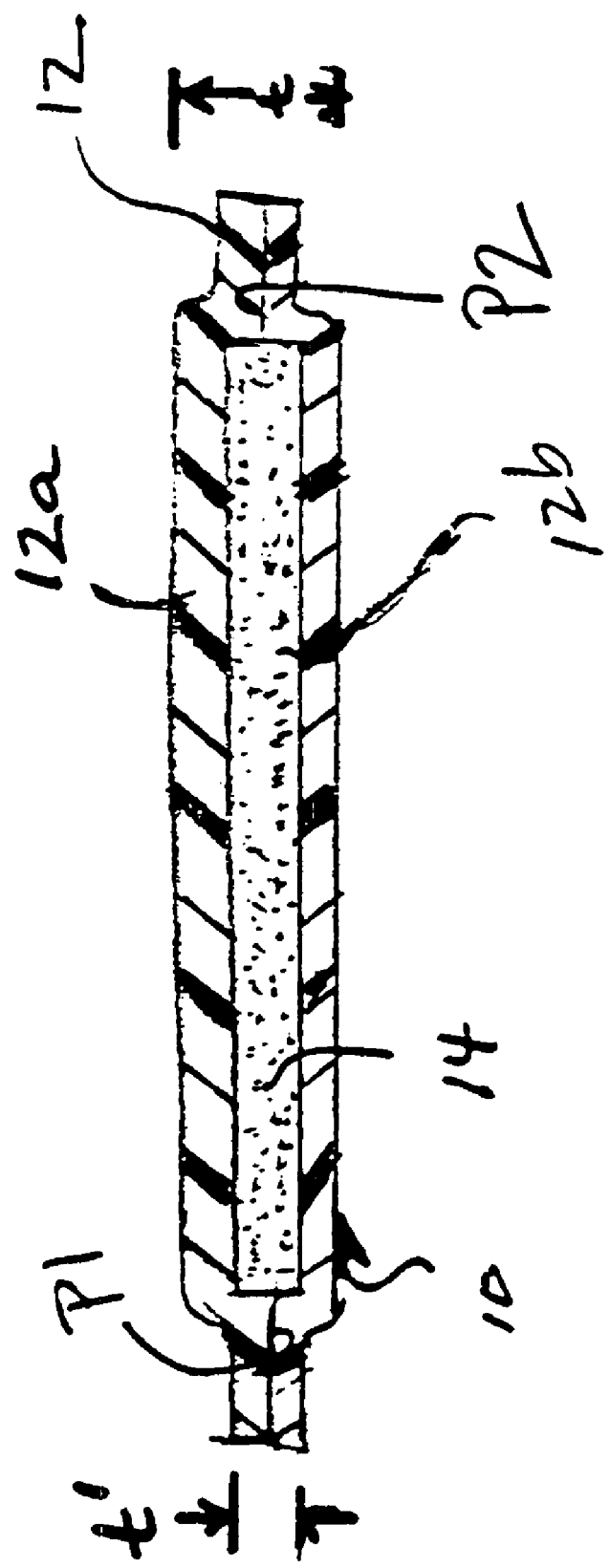
FIG. 4 is a cross-sectional view taken along line 4-4 of FIG. 1.

As shown in FIGS. 1 and 4, the device 10 of this invention comprises a packet 12 containing a sheet of absorbent material. Either sheet 14 (FIG. 2) or sheet 14a (FIG. 3) may be used. The sheet 14 is depicted contained within the packet 12 in FIGS. 1 and 4. These sheets 14 and 14a are most advantageously tissue paper. The packet 12 may have an overall rectangular configuration with a length l of from about 3 to about 6 inches and a width w of from about 3 to about 6 inches. Its thickness t (FIG. 4) is typically less than about 1/4 inch, and may range from about 1/8 to about 3/8 inch.

The sheet of absorbent material, either sheets 14 or 14a, may also have an overall rectangular configuration, but its length l' and width w' dimensions are less than those of the packet 12, and its thickness t'(FIG. 4) is less than about 1/8 inch, typically from about 1/16 to about 1/8 inch. As depicted by the sheet 14 shown in FIG. 2, the entire sheet of absorbent material may be soaked or impregnated with a liquid solution used to test for the presence of occult blood in feces. Or, as illustrated by the sheet 14a shown in FIG. 3., only a portion of the sheet, such as, for example, a central, circular target zone 14a, may be impregnated with the liquid testing solution. Typically, the liquid soaked paper weighs from about 2 to about 4 grams.

The liquid testing solution includes a guaiac material and hydrogen peroxide. The main ingredients of this solution are from about 3 to about 8 weight percent hydrogen peroxide, from about 60 to about 80 weight percent alcohol, preferably ethanol, and from about 12 to about 37 weight percent guaiac material. The following is an example of a typical solution used to impregnate the sheets 14 and 14a:

EXAMPLE

A testing solution includes 5 weight percent hydrogen peroxide, 75 weight percent denatured ethanol, and the balance guaiac material.

In accordance with this invention, essentially immediately after impregnating the sheet 14 or 14a with the liquid testing solution, the wet sheet is sealed within the packet 12. Any detrimental amount of air is evacuated from the packet 12 using a vacuum as the solution soaked sheet 14 or 14a, as the case may be, is sealed within the packet 12. The packet 12 is formed from two substantially the same sized, thin layers 12a and 12b of an opaque substance that is essentially impermeable to light and air. The layers 12a and 12b, preferably aluminum foil, each have a thickness of less than about 1/16 inch.

The two layers 12a and 12b are placed one on top of the other so that the layer 12a overlies and completely covers the layer 12b, with the sheet 14 or 14a, as the case may be, sandwiched between them. The layers 12a and 12b each have outer, rectangular marginal edge portions P1 and P2, respectively, defining a layer's perimeter. These marginal edge portions P1 and P2 are adjoining and sealed together to prevent the liquid solution in the absorbent material from escaping the packet 12 until the packet is opened to use the impregnated sheet 14 or 14a, as the case may be. Any detrimental amount of air initially present between the layers 12a and 12b is evacuated therefrom by a vacuum using conventional vacuum packaging techniques.

Preferably, small corner portions C1 and C2 opposite each other, respectively, of the layers 12a and 12b, are not sealed together. These unsealed corner portions C1 and C2 facilitate opening the packet 12 to remove the solution soaked sheet 14 or 14a from the packet. Though the corner portions C1 and C2 are not seal together, the packet 12 remains sealed until the layers 12a and 12b are manually separated by tearing or pulling them apart. When this is done, the solution soaked sheet 14 or 14a, as the case may be, is withdrawn from the opened packet 12 and used almost immediately to collect thereon a sample of feces. If occult blood is presence in the sample, the color blue appears on the solution soaked sheet 14 or 14a almost instantaneously upon contact with the sample.

SCOPE OF THE INVENTION

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover all modifications and alternate constructions coming within the spirit and scope of the invention as generally expressed by the following claims, which particularly point out and distinctly claim the subject matter of the invention:

The invention claimed is:

1. A method of detecting the presence of occult blood in feces, comprising the steps of
   (a) providing a sheet of absorbent material impregnated with a liquid solution that reacts with feces to produce a color change when blood is present, said liquid solution comprising a mixture of a guaiac material and a peroxide,
   (b) placing said sheet absorbent in a packet and subsequently evacuating the packet to remove air therefrom and sealing the packet to prevent the liquid solution from escaping the packet until opened to use the impregnated sheet of absorbent material, said evacuated and sealed packet being essentially impermeable to light and air,
   (c) manually opening the packet and removing the impregnated sheet of absorbent material, and
   (d) collecting a sample of feces on the impregnated sheet of absorbent material, a color change appearing on the impregnated sheet of absorbent material in the presence of occult blood.

2. The method of claim 1 where the liquid solution comprises
   from 3 to 8 weight percent hydrogen peroxide,
   from 60 to 80 weight percent alcohol,
   from 12 to 37 weight percent guaiac material.

3. The method of claim 1 where the sheet of absorbent material is tissue paper.

4. The device of claim 1 where the substance from which the packet is made is aluminum foil.

5. A device for detecting the presence of occult blood in feces, comprising
   a sealed and evacuated packet containing a sheet of absorbent material impregnated with a liquid solution of a guaiac material and a peroxide, said sheet being impregnated with the liquid solution prior to the packet being sealed and evacuated, so opening the packet or otherwise manipulating the packet does not mix the guaiac material and peroxide, which has already been premixed,
   said packet comprising two overlying layers, each having outer edge portions defining a layer's perimeter, said outer edge portions of the layers adjoining and being sealed together to prevent the liquid solution from escaping the packet until opened to use the impregnated sheet of material, any detrimental air between the layers being evacuated therefrom by vacuum, and
   said layers being made of a substance that is essentially impermeable to light and air.

6. A device for detecting the presence of occult blood in feces, comprising
   a sealed and evacuated packet containing a sheet of absorbent tissue paper impregnated with a liquid solution comprising from 3 to 8 weight percent hydrogen peroxide, from 60 to 80 weight percent alcohol, and from 12 to 37 weight percent guaiac material, said sheet being impregnated with the liquid solution prior to the packet being sealed and evacuated, said packet comprising two overlying layers with said sheet sandwiched between said layers, said layers each having outer edge portions defining a layer's perimeter, said outer edge portions of the layers adjoining and being sealed together to prevent the liquid solution from escaping the packet until opened to use the impregnated sheet of material, any detrimental air between the layers being evacuated therefrom by vacuum, and said layers being made of aluminum foil that is essentially impermeable to light and air and that has a thickness of less than 1/16 inch.

\* \* \* \* \*